(12) United States Patent
McIntosh et al.

(10) Patent No.: US 9,642,571 B2
(45) Date of Patent: *May 9, 2017

(54) SYSTEM AND METHOD FOR SENSORIZED USER INTERFACE

(71) Applicant: Orthosensor Inc., Dania Beach, FL (US)

(72) Inventors: Jason McIntosh, Eden Prarie, MN (US); Martin Roche, Fort Lauderdale, FL (US); Marc Boillot, Plantation, FL (US); Carlos Gil, Jacksonville, FL (US)

(73) Assignee: ORTHOSENSOR INC, Dania Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/957,484

(22) Filed: Dec. 2, 2015

(65) Prior Publication Data

US 2016/0143577 A1  May 26, 2016

(51) Int. Cl.
| | |
|---|---|
| *G08B 3/00* | (2006.01) |
| *A61B 5/00* | (2006.01) |
| *G06F 3/01* | (2006.01) |
| *G06F 3/03* | (2006.01) |
| *G06F 3/0485* | (2013.01) |
| *H04R 25/00* | (2006.01) |
| *G06F 3/0488* | (2013.01) |
| *G06F 3/0346* | (2013.01) |
| *A61B 5/103* | (2006.01) |
| *A61B 8/08* | (2006.01) |
| *H04L 29/08* | (2006.01) |
| *A61B 5/11* | (2006.01) |

(52) U.S. Cl.
CPC .............. *A61B 5/45* (2013.01); *A61B 5/0002* (2013.01); *A61B 5/0024* (2013.01); *A61B 5/1036* (2013.01); *A61B 5/1126* (2013.01); *A61B 5/742* (2013.01); *A61B 8/0841* (2013.01); *G06F 3/017* (2013.01); *G06F 3/0304* (2013.01); *G06F 3/0346* (2013.01); *G06F 3/0485* (2013.01); *G06F 3/04883* (2013.01); *H04L 67/12* (2013.01); *H04R 25/502* (2013.01); *A61B 5/002* (2013.01); *A61B 2562/0219* (2013.01)

(58) Field of Classification Search
CPC ....... G06F 3/016; G06F 3/0304; G06F 3/0485
USPC ...... 340/686.1, 573.1, 539.1, 539.12; 482/8; 602/16, 587
See application file for complete search history.

(56) References Cited

U.S. PATENT DOCUMENTS

| | | |
|---|---|---|
| 5,274,363 A | 12/1993 | Koved |
| 6,090,114 A | 7/2000 | Matsuno et al. |
| 6,130,663 A | 10/2000 | Null |

(Continued)

*Primary Examiner* — Daryl Pope

(57) ABSTRACT

A system and method for is provided for operation of an orthopedic system. The system includes a load sensor for converting an applied pressure associated with a force load on an anatomical joint, and an inertial sensing device configured to measure alignment. The inertial sensing device provides alignment measurement data to measure alignment. An ultrasonic transducer, MEMs microphone, electromagnets, optical elements, metallic objects or other transducers can be configured to convert or convey a physical movement to an electrical signal and support measurement of muscular-skeletal alignment. The load sensor can be used to measure load magnitude and position of load of an applied load by the muscular-skeletal system.

20 Claims, 11 Drawing Sheets

(56) References Cited

U.S. PATENT DOCUMENTS

| | | |
|---|---|---|
| 6,137,427 A | 10/2000 | Binstead |
| 6,313,825 B1 | 11/2001 | Gilbert |
| 6,546,277 B1 | 4/2003 | Franck et al. |
| 6,937,227 B2 | 8/2005 | Qamhiyah |
| 7,078,911 B2 | 7/2006 | Cehelnik |
| 7,081,884 B2 | 7/2006 | Kong |
| 7,092,109 B2 | 8/2006 | Satoh |
| 7,130,754 B2 | 10/2006 | Satoh |
| 7,139,418 B2 | 11/2006 | Abovitz et al. |
| 7,309,339 B2 | 12/2007 | Cusick |
| 7,392,076 B2 | 6/2008 | Moctezuma de la Barrera |
| 7,395,181 B2 | 7/2008 | Foxlin |
| 7,477,926 B2 | 1/2009 | McCombs |
| 7,559,931 B2 | 7/2009 | Stone et al. |
| 7,604,645 B2 | 10/2009 | Barzell et al. |
| 7,636,595 B2 | 12/2009 | Marquart |
| 7,657,298 B2 | 2/2010 | Moctezuma de la Barrera et al. |
| 7,660,623 B2 | 2/2010 | Hunter et al. |
| 7,681,448 B1 | 3/2010 | Preston et al. |
| 7,685,861 B2 | 3/2010 | Lynch et al. |
| 7,689,032 B2 | 3/2010 | Strassenburg-Kleciak |
| 7,771,436 B2 | 8/2010 | Moctezuma et al. |
| 7,824,328 B2 | 11/2010 | Gattani et al. |
| 7,993,289 B2 | 8/2011 | Quistgaard et al. |
| 8,777,877 B2 * | 7/2014 | Stein .................... A61B 17/025 600/587 |
| 2001/0011175 A1 | 8/2001 | Hunter et al. |
| 2003/0132913 A1 | 7/2003 | Issinski |
| 2004/0024309 A1 | 2/2004 | Ferre et al. |
| 2004/0236424 A1 | 11/2004 | Berez et al. |
| 2004/0254584 A1 | 12/2004 | Sarin et al. |
| 2005/0154431 A1 | 7/2005 | Quistgaard et al. |
| 2006/0092022 A1 | 5/2006 | Cehelnik |
| 2006/0161870 A1 | 7/2006 | Huppi |
| 2006/0161871 A1 | 7/2006 | Hotelling |
| 2006/0164241 A1 | 7/2006 | Makela |
| 2006/0224429 A1 | 10/2006 | Mathew |
| 2006/0235420 A1 | 10/2006 | Irving |
| 2007/0127039 A1 | 6/2007 | Njolstad |
| 2007/0175489 A1 | 8/2007 | Moctezuma et al. |
| 2008/0269596 A1 | 10/2008 | Revie et al. |
| 2008/0269599 A1 | 10/2008 | Csavoy et al. |
| 2009/0318836 A1 | 12/2009 | Stone et al. |
| 2010/0063508 A1 | 3/2010 | Borja et al. |
| 2010/0069911 A1 | 3/2010 | Borja et al. |
| 2010/0076505 A1 | 3/2010 | Borja et al. |
| 2010/0137869 A1 | 6/2010 | Borja et al. |
| 2010/0160771 A1 | 6/2010 | Gielen et al. |
| 2010/0210939 A1 | 8/2010 | Hartmann et al. |

* cited by examiner

100

190

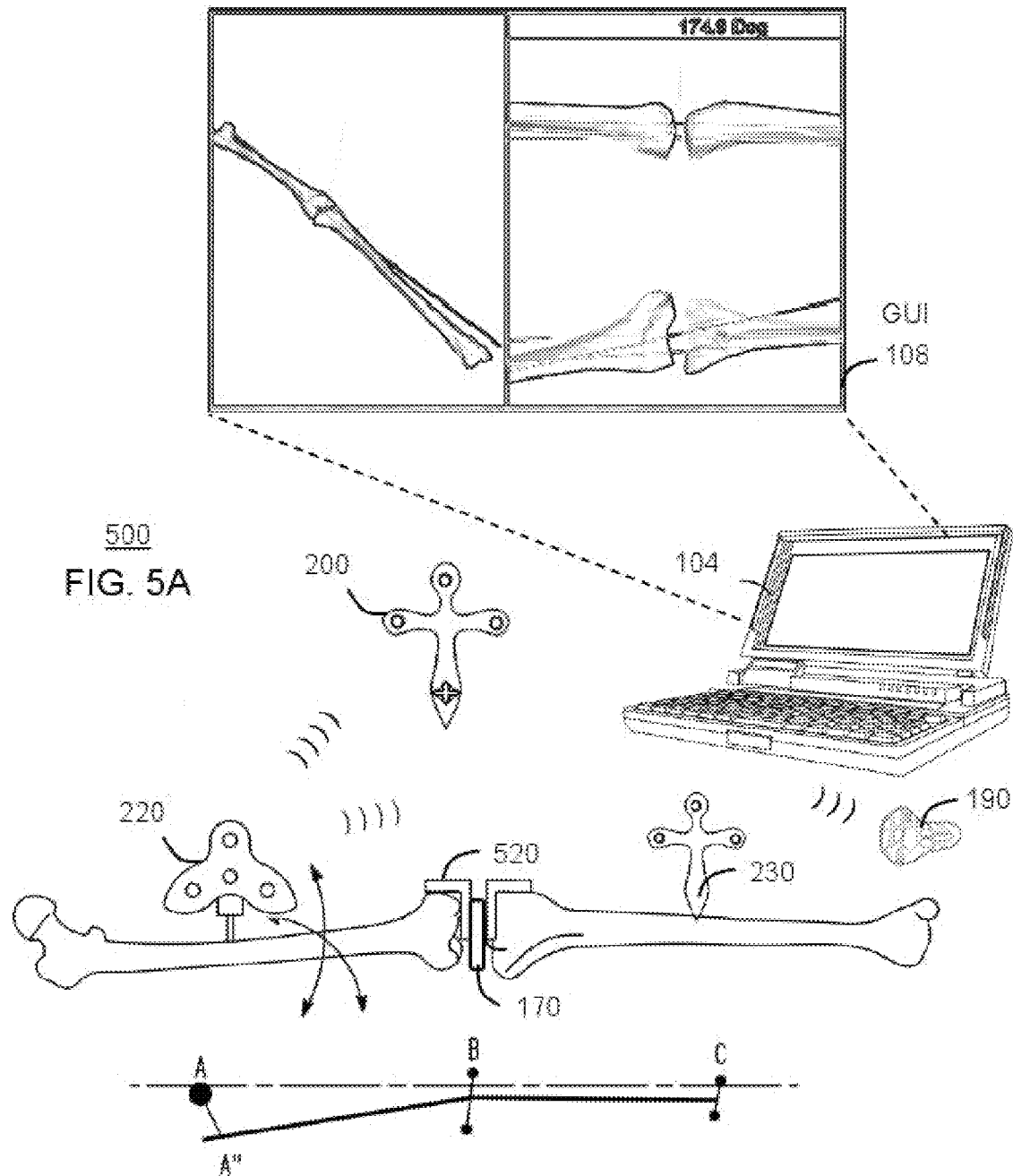

SYSTEM AND METHOD FOR SENSORIZED USER INTERFACE

CROSS-REFERENCE TO RELATED APPLICATION

This application is a Continuation of U.S. patent application Ser. No. 13/850,262 filed on Mar. 25, 2013 the entire contents of which are hereby incorporated by reference. The application Ser. No. 13/850,262 is a continuation of U.S. patent application Ser. No. 13/164,396 filed on Jun. 20, 2011 which is now U.S. Pat. No. 8,421,642 issued on Apr. 16, 2011 the entire contents of which are hereby incorporated by reference. The application Ser. No. 13/164,396 is a continuation in part of U.S. patent application Ser. No. 11/844,329 filed on Aug. 23, 2007 which is now U.S. Pat. No. 7,978,091 issued on Jul. 12, 2011 the entire contents of which are hereby incorporated by reference. The application Ser. No. 11/844,329 is a Non-provisional Patent Application of Provisional Patent Application 60/839,742 filed on Aug. 24, 2006 the entire contents of which are hereby incorporated by reference.

BACKGROUND

The present embodiments of the invention generally relate to the field of electronic accessory devices, and more particularly to sensors and input pointing devices. Medical systems and other sensing technologies are generally coupled to a display. Interaction with the display can occur via mouse, keyboard or touch screen. There are times when audible feedback is advantageous.

BRIEF DESCRIPTION OF DRAWINGS

FIG. 5A is an illustration of an orthopedic navigation system for assessing cutting jig orientation and reporting anatomical alignment in accordance with one embodiment;

DETAILED DESCRIPTION

Figure 1A:
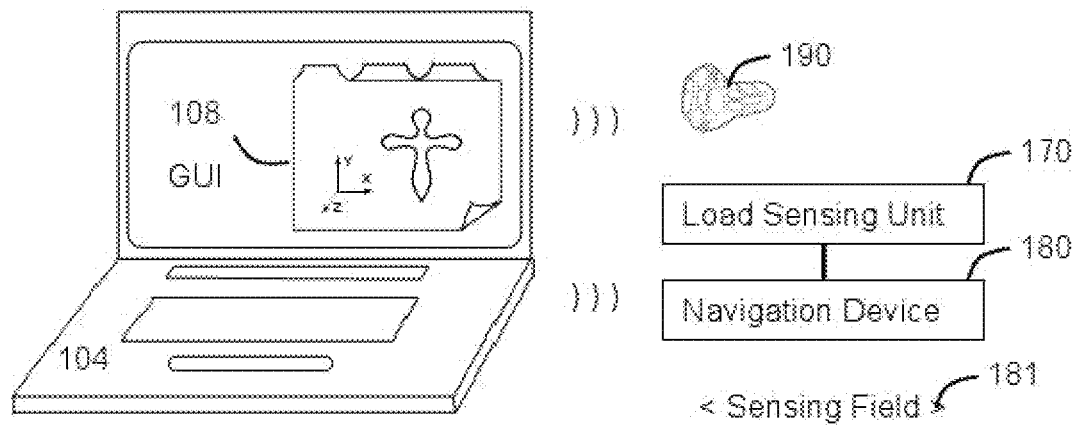
FIG. 1A is an illustration of a graphical user interface of a system and earpiece to provide audio feedback in accordance with one embodiment.

While the specification concludes with claims defining the features of the invention that are regarded as novel, it is believed that the invention will be better understood from a consideration of the following description in conjunction with the drawing figures, in which like reference numerals are carried forward.

Broadly stated, a system and method is provided having both user interface and orthopedic parameter measurement capability. In one embodiment, the system provides quantitative measurements of muscular-skeletal system and insertion of prosthetic components. A navigation portion of the system provides user interface control via one or more wand pointing devices and a receiver device. The wand can be used to identify points of interest in three-dimensional space and for user input. The system can incorporate user feedback in the context of a surgical work-flow. The wand can also be affixed to an object to track its movement and orientation within proximity of the receiver. A measurement portion of the system includes sensors for measuring a parameter of the muscular-skeletal system. An example of parameter measurement is a force, pressure, alignment or load measurement. In one embodiment, the sensors reside in a prosthetic component of an artificial joint system. The prosthetic component when installed provides quantitative measurement data that can be used to assess the knee joint. Sensory feedback and guidance provides audio and visual indication of work flow steps and the wand's location and orientation.

Referring to FIG. 1A, an exemplary medical system 100 for measuring, assessing, and reporting quantitative data is shown. In a non-limiting example, system 100 can measure parameters of the muscular-skeletal system while simultaneously providing position and alignment information. The medical system 100 includes a graphical user interface (GUI) 108, a load sensing unit 170 and a navigation device 180 wirelessly coupled thereto. The load sensing unit 170 provides a measure of applied force and can be used to measure load balance. In one embodiment, load sensing unit 170 is housed in a prosthetic component for trial measurement. The surgical navigation device 180 projects an ultrasonic sensing field 181 and adjusts its energy and range based on a proximity of its component devices, and with respect to the load sensing unit 170. It measures and reports an alignment that corresponds to the load magnitude and load balance measurements reported by the load sensing unit 170.

The load sensing unit 170 converts a force applied thereto within an anatomical joint into an electric signal, for example, by way of polymer sensing, piezoelectric transduction, or ultrasonic waveguide displacement to measure a load balance of the force. The load and alignment indicators presented in the GUI 108 provide quantitative feedback of the measured parameters during a work flow. The system 100 also includes an earpiece 190 that audibly presents an indicator of the alignment and the load balance responsive to completion of one or more work flow steps of the surgical procedure. The work flow steps are, for example, associated with the identifying and tracking three-dimensional (3D) points in the ultrasonic sensing field 181, for instance, an anatomical location or instrument orientation. One example of a navigation system and user interface for directing a control action is disclosed in U.S. patent application Ser. No. 12/900,878, the entire contents of which are hereby incorporated by reference.

A remote system 104 serves as a display that is wirelessly coupled to the surgical navigation device 180 and graphically presents information related to the load balance and alignment via the GUI 108. Remote system 104 can be placed outside of the sterile field of an operating room but within viewing range of the medical staff. In one embodiment, remote system is a laptop computer. Alternatively, remote system 104 can be an application specific equipment that comprises a display and a processor, including but not limited to, a mobile device. Remote system 104 can display the work flow with measurement data for assessment. Remote system 104 can include a processor to analyze the quantitative measurement data to provide feedback during a procedure that can be visual, audible, or haptic.

Figure 1B:
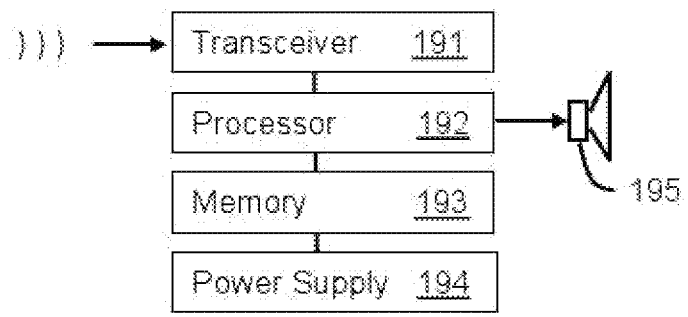
FIG. 1B is a block diagram of the earpiece in accordance with one embodiment.

Referring to FIG. 1B, a block diagram of the earpiece 190 is shown. The earpiece 190 provides audio feedback of parameters reported by the load sensing unit 170, the navigation device 180 and the GUI 108. The earpiece 190 can include a transceiver 191 that can support singly or in combination any number of wireless access technologies including without limitation Bluetooth, Wireless Fidelity (WiFi), ZigBee and/or other short or long range radio frequency communication protocols. The transceiver 191 can also provide support for dynamic downloading over-the-air to the earpiece 190. Next generation access technologies can also be applied to the device. The processor 192 can utilize computing technologies such as a microprocessor, Application Specific Integrated Chip (ASIC), and/or digital signal processor (DSP) with associated storage memory 193 such a Flash, ROM, RAM, SRAM, DRAM or other like technologies for controlling operations of the earpiece device 190. The processor 192 can also include a clock to record a time stamp. The speaker 195 can couple to the processor 192 through an analog to digital converter or a general processor input/output (GPIO) pin for providing acoustic feedback, for example, audio beeps or other audible indications. The power supply 194 can utilize common power management technologies such as replaceable batteries, supply regulation technologies, and charging system technologies for supplying energy to the components of the earpiece 190 and to facilitate portable applications. The remote system 104 can also provide power for operation or recharging via USB or direct coupling of the earpiece 190.

Figure 2:
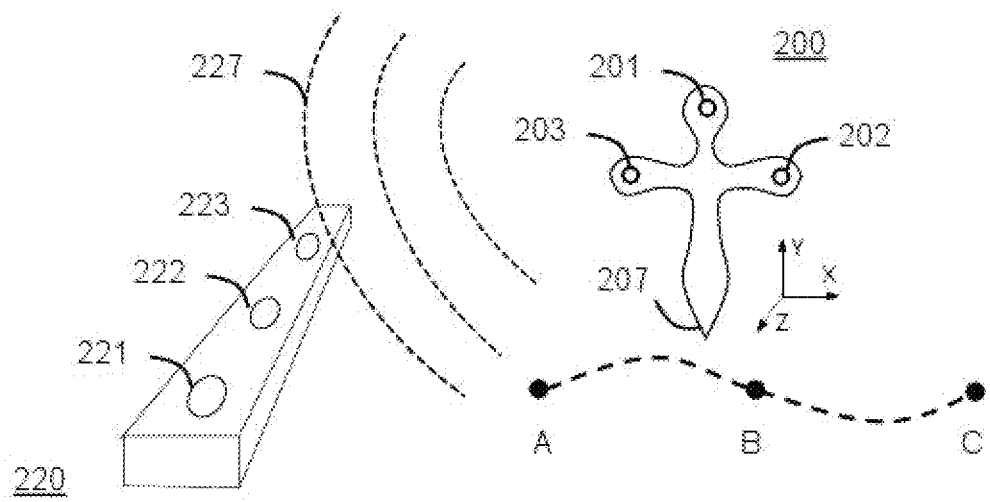
FIG. 2 is an illustration a receiver and wand component of the navigation system in accordance with one embodiment.

Referring to FIG. 2, exemplary components of the navigation device 180 are shown, specifically, a wand 200 and a receiver 220 for creating the three-dimensional ultrasonic sensing field. The wand 200 is a hand-held device with a size dimension of approximately 8-10 cm in width, 2 cm depth, and an extendable length from 10-12 cm. The receiver 220 has size dimensions of approximately 1-2 cm width, 1-2 cm depth, and a length of 4 cm to 6 cm. Neither device is however limited to these dimensions and can be altered to support various functions (e.g, hand-held, coupled to object). The current size permits ultrasonic tracking of the wand tip with millimeter spatial accuracy up to approximately 2 m in distance. Not all the components shown are required; fewer components can be used depending on required functionality, for instance, whether the wand is used for isolated point registration, continuous wand tracking without user input or local illumination, or as integrated devices (e.g., laptop display).

The wand 200 includes sensors 201-203 and a wand tip 207. The sensors can be ultrasonic transducers, Micro Electro Mechanical Element (MEMS) microphones, electromagnets, optical elements (e.g., infrared, laser), metallic objects or other transducers for converting or conveying a physical movement to an electric signal such as a voltage or current. They may be active elements in that they are self powered to transmit signals, or passive elements in that they are reflective or exhibit detectable magnetic properties. The wand 200 is used to register points of interest (see points A, B, C), for example, along a contour of an object or surface, which can be presented in a user interface (see remote system 104 FIG. 1A). As will be discussed ahead, the wand 200 and receiver 220 can communicate via ultrasonic, infrared and electromagnetic sensing to determine their relative location and orientation to one another. Other embodiments incorporating accelerometers to provide further positional information is discussed in U.S. patent application Ser. No. 12/982,944 filed Dec. 31, 2010 the entire contents of which are incorporated by reference.

In one embodiment, the wand 200 comprises three ultrasonic transmitters 201-203 each can transmit ultrasonic signals through the air, an electronic circuit (or controller) 214 for generating driver signals to the three ultrasonic transmitters 201-203 for generating the ultrasonic signals, a user interface 218 (e.g., button) that receives user input for performing short range positional measurement and alignment determination, a communications port 216 for relaying the user input and receiving timing information to control the electronic circuit 214, and a battery 215 for powering the electronic circuitry of wand 200. The wand 200 may contain more or less than the number of components shown; certain component functionalities may be shared as integrated devices.

The wand tip 207 identifies points of interest on a structure, for example, an assembly, object, instrument or jig in three-dimensional space, though is not so limited. The wand tip 207 does not require sensors since its spatial location in three-dimensional space is established by the three ultrasonic transmitters 201-203 arranged at the cross ends. However, a sensor element can be integrated on the tip 207 to provide ultrasound capabilities (e.g., structure boundaries, depth, etc.) or contact based sensing. In such case, the tip 207 can be touch sensitive to registers points responsive to a physical action, for example, touching the tip to an anatomical or structural location. The tip can comprise a mechanical or actuated spring assembly for such purpose. In another arrangement it includes a capacitive touch tip or electrostatic assembly for registering touch. The wand tip 207 can include interchangeable, detachable or multi-headed stylus tips for permitting the wand tip to identify anatomical features while the transmitters 201-203 remain in line-of-sight with the receiver 220 (see FIG. 1A). These stylus tips may be right angled, curved, or otherwise contoured in fashion of a pick to point to difficult to touch locations. This permits the wand to be held in the hand to identify via the tip 207, points of interest such as (anatomical) features on the structure, bone or jig. One such example of an ultrasonic navigation system is disclosed and derived from U.S. Pat.

No. 7,725,288 and application Ser. No. 12/764,072 filed Apr. 20, 2010 the entire contents of which are hereby incorporated by reference.

The user interface 218 can include one or more buttons to permit handheld operation and use (e.g., on/off/reset button) and illumination elements to provide visual feedback. In one arrangement, a 5-state navigation press button 209 can communicate directives to further control or complement the user interface. It can be ergonomically located on a side of the wand to permit single handed use. The wand 200 may further include a haptic module with the user interface 218. As an example, the haptic module may change (increase/decrease) vibration to signal improper or proper operation. The wand 200 includes material coverings for the transmitters 201-202 that are transparent to sound (e.g., ultrasound) and light (e.g., infrared) yet impervious to biological material such as water, blood or tissue. In one arrangement, a clear plastic membrane (or mesh) is stretched taught; it can vibrate under resonance with a transmitted frequency. The battery 215 can be charged via wireless energy charging (e.g., magnetic induction coils and super capacitors).

The wand 200 can include a base attachment mechanism 205 for coupling to a structure, object or a jig. As one example, the mechanism can be a magnetic assembly with a fixed insert (e.g., square post head) to permit temporary detachment. As another example, it can be a magnetic ball and joint socket with latched increments. As yet another example, it can be a screw post or pin to a screw. Other embodiments may permit sliding, translation, rotation, angling and lock-in attachment and release, and coupling to standard jigs by way of existing notches, ridges or holes.

The wand 200 can further include an amplifier 213 and the accelerometer 217. The amplifier enhances the signal to noise ratio of transmitted or received signals. The accelerometer 217 identifies 3 and 6 axis tilt during motion and while stationary. The communications module 216 may include components (e.g., synchronous clocks, radio frequency 'RF' pulses, infrared 'IR' pulses, optical/acoustic pulse) for signaling to the receiver 220 (FIG. 2B). The controller 214, can include a counter, a clock, or other analog or digital logic for controlling transmit and receive synchronization and sequencing of the sensor signals, accelerometer information, and other component data or status. The battery 215 powers the respective circuit logic and components. The infrared transmitter 209 pulses an infrared timing signal that can be synchronized with the transmitting of the ultrasonic signals (to the receiver).

Additional ultrasonic sensors can be included to provide an over-determined system for three-dimensional sensing. The ultrasonic sensors can be MEMS microphones, receivers, ultrasonic transmitters or combination thereof. As one example, each ultrasonic transducer can perform separate transmit and receive functions. One such example of an ultrasonic sensor is disclosed in U.S. Pat. Nos. 7,414,705 and 7,724,355 the entire contents of which are hereby incorporated by reference. The ultrasonic sensors can transmit pulse shaped waveforms in accordance with physical characteristics of a customized transducer for constructing and shaping waveforms.

The controller 214 can utilize computing technologies such as a microprocessor (uP) and/or digital signal processor (DSP) with associated storage memory 208 such a Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm. The controller can be an embedded platform running one or more modules of an operating system (OS). In one arrangement, the storage memory may store one or more sets of instructions (e.g., software) embodying any one or more of the methodologies or functions described herein.

The receiver 220 comprises a processor 233 for generating timing information, registering a pointing location of the wand 200 responsive to the user input, and determining short range positional measurement and alignment from three or more pointing locations of the wand 200 with respect to the receiver 220. It includes a communications interface 235 for transmitting the timing information to the wand 200 that in response transmits the first, second and third ultrasonic signals. The ultrasonic signals can be pulse shaped signals generated from a combination of amplitude modulation, frequency modulation, and phase modulation. Three microphones 221-223 each receive the first, second and third pulse shaped signals transmitted through the air. The receiver 220 shape can be configured from lineal as shown, or in more compact arrangements, such as a triangle shape. The receiver 220 can also include an attachment mechanism 240 for coupling to bone or a jig. As one example, the mechanism 240 can be a magnetic assembly with a fixed insert (e.g., square post head) to permit temporary detachment. As another example, it can be a magnetic ball and joint socket with latched increments.

The receiver 220 can further include an amplifier 232, the communications module 235, an accelerometer 236, and processor 233. The processor 233 can host software program modules such as a pulse shaper, a phase detector, a signal compressor, and other digital signal processor code utilities and packages. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 identifies axial tilt (e.g., 3/6 axis) during motion and while stationary. The battery 234 powers the respective circuit logic and components. The receiver includes a photo diode 241 for detecting the infrared signal and establishing a transmit time of the ultrasonic signals to permit wireless infrared communication with the wand. The receiver 200 may contain more or less than the number of components shown; certain component functionalities may be shared or therein integrated.

The communications module 235 can include components (e.g., synchronous clocks, radio frequency 'RF' pulses, infrared 'IR' pulses, optical/acoustic pulse) for local signaling (to wand 200). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplated, it should be noted that the receiver 220 can include a user interface 237 to permit standalone operation. As one example, it can include 3 LED lights comprising an indicator 224 to show three or more wand tip pointing location alignment status. The user interface 237 may also include a touch screen or other interface display with its own GUI for reporting positional information and alignment.

The processor 233 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein. A timer can be clocked within the processor 233 or externally.

The wireless communication interface (Input/Output) 239 wirelessly conveys the positional information and the short range alignment of the three or more pointing locations to a remote system. The remote system can be a computer, laptop or mobile device that displays the positional information and alignment information in real-time as described ahead. The battery 234 powers the processor 233 and associated electronics on the receiver 220. The sensor 228 can measure air flow (or speed) of the air flowing through the device in a defined time segment. It can also be coupled to a tube (not shown) for more accurately measuring acoustic impedance. The thermistor 229 measures ambient air temperature in fractional units and can report an analog value within a tuned range (e.g., 30 degree span) that can be digitized by the processor 233. One example of a device for three-dimensional sensing is disclosed in U.S. patent application Ser. No. 11/683,410 entitled "Method and Device for Three-Dimensional Sensing" filed Mar. 7, 2007 the entire contents of which are hereby incorporated by reference.

In a first arrangement, the receiver 220 is wired via a tethered electrical connection (e.g., wire) to the wand 200. That is, the communications port of the wand 200 is physically wired to the communications interface of the receiver 220 for receiving timing information. The timing information from the receiver 220 tells the wand 200 when to transmit and includes optional parameters that can be applied to pulse shaping. The processor 233 on the receiver 220 employs this timing information to establish Time of Flight measurements in the case of ultrasonic signaling with respect to a reference time base.

In a second arrangement, the receiver 220 is communicatively coupled to the wand 200 via a wireless signaling connection. An infrared transmitter 209 on the wand 200 transmits an infrared timing signal with each transmitted pulse shaped signal. Wand 200 pulses an infrared timing signal that is synchronized with the transmitting of the ultrasonic signals to the receiver 220. The receiver 220 can coordinate the emitting and the capturing of the plurality of ultrasonic pulses via wireless infrared synchronized communication from the wand 200. The receiver 220 can include a photo diode 241 for determining when the infrared timing signal is received. In this case the communications port of the wand 200 is wirelessly coupled to the communications interface of the receiver 220 by way of the infrared transmitter and the photo diode 241 for relaying the timing information to within microsecond accuracy (~1 mm resolution). The processor 233 on the receiver 220 employs this infrared timing information to establish the first, second and third Time of Flight measurements with respect to a reference transmit time.

Figure 3:
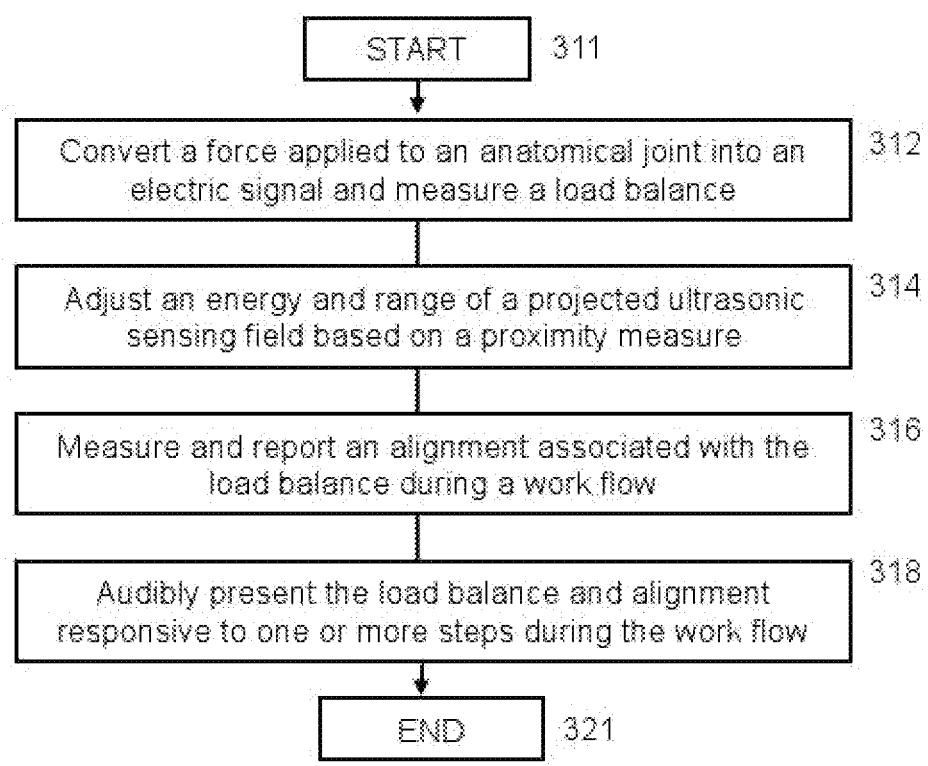
FIG. 3 is an exemplary method for audio feedback of load balance and alignment with the navigation system in accordance with one embodiment.

Referring to FIG. 3, a method 300 for navigated system operation providing audio feedback is shown. The method 300 can be practiced with more or less than the number of steps shown. To describe the method 300, reference will be made to FIGS. 1-2, 4 and 5 although it is understood that the method 300 can be implemented in any other suitable device or system using other suitable components. Moreover, the method 300 is not limited to the order in which the steps are listed. In addition, the method 300 can contain a greater or a fewer number of steps than those shown in FIG. 3.

The method 300 can start at step 311 after the surgical work flow has commenced and the navigation system has been calibrated and configured. The remote system 104 visually presents the GUI and provides work-flow visual guidance and audio content during the surgical procedure. One example of a workflow user interface is disclosed in U.S. patent application Ser. No. 12/901,094 entitled "Orthopedic Navigation System with Sensorized Devices" filed Oct. 8, 2010 the entire contents of which are hereby incorporated by reference. The referenced disclosure above provides reference work steps to a total knee replacement surgery that can be used as example to the method 300 herein.

At step 312, an applied anatomical force within an anatomical joint, such as the knee, can be converted into an electric signal, for example, by way of piezoelectric transduction to measure a load balance of the applied anatomical force in the joint. The conversion can be performed and reported by the load sensing unit 170 previously shown in FIG. 1A. The load sensing unit is an integrated wireless sensing module comprising an i) encapsulating structure that supports sensors and contacting surfaces and ii) an electronic assemblage that integrates a power supply, sensing elements, transducers, biasing spring or springs or other form of elastic members, an accelerometer, antennas and electronic circuitry that processes measurement data as well as controls all operations of energy conversion, propagation, detection and wireless communications. One exemplary method of wireless parameter sensing and reporting is disclosed in U.S. patent application Ser. No. 12/825,724 filed Jun. 29, 2010 the entire contents of which are hereby incorporated by reference. In yet other arrangements, the load sensing unit 170 can include piezoelectric, capacitive, optical or temperature sensors or transducers to measure the compression or displacement. It is not limited to ultrasonic transducers and waveguides. One exemplary method of force sensing is disclosed in U.S. patent application Ser. No. 12/826,329 filed Jun. 29, 2010 the entire contents of which are hereby incorporated by reference.

At a step 314, an energy and range of a projected ultrasonic sensing field is adjusted based on a proximity measurement. In general, the navigation system can be used to measure a mechanical axis of the muscular-skeletal system. In the example, the mechanical axis corresponds to the position of the femur and tibia in relation to one another. The mechanical axis is used for determining bone cut angles for receiving prosthetic components. Human anatomy can vary substantially over a large population. For example, the energy can be increased thereby extending the range of the ultrasonic sensing field for measuring position and alignment of a tall patient. Conversely, the energy can be decreased when devices are positioned in close proximity to prevent overloading transducers with a large signal.

At a step 316, a report is generated from quantitative measurements related to alignment and load. Measurements on load magnitude, load balance, and alignment are included. The report can indicate load magnitude and load balance over a range of motion for the alignment. The remote system provides visualization of the alignment and load measurements to support the prosthetic component installation. Moreover, the remote system can process the quantitative data to project outcomes based on the information.

At a step 318, an audible signal can be sent to the ear piece that presents the load balance and alignment. The audible presentation can provide feedback to the surgeon during one or more steps of the work flow. Along with provided visualization, the audible signal can aid or support the translation of quantitative data to the subjective feel or tactile feedback present when the surgeon works on and moves the prosthetic components. At step 321, the method 300 can end.

Figure 4:
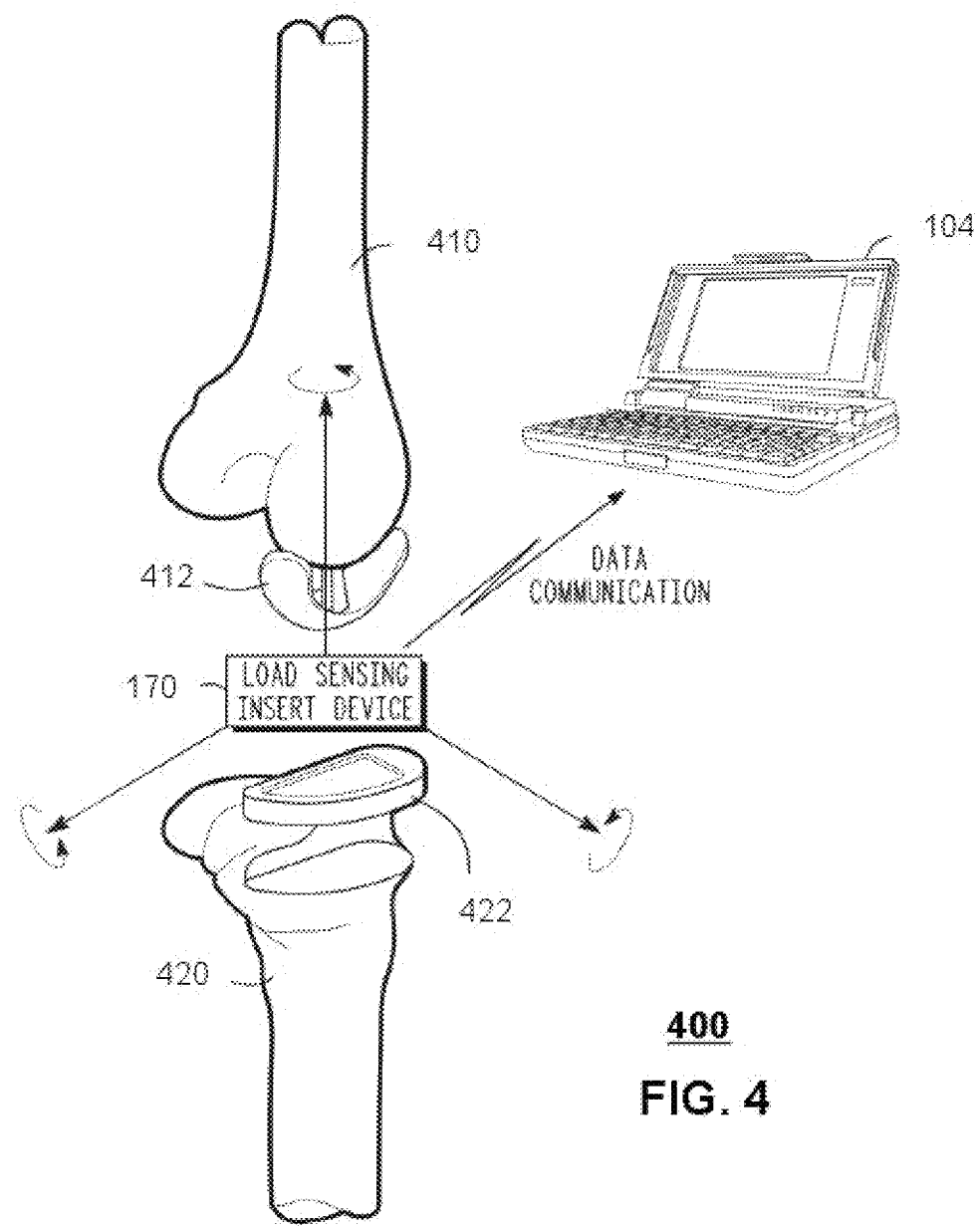
FIG. 4 is an illustration of a load sensing unit placed in a joint of the muscular-skeletal system for measuring a load parameter in accordance with one embodiment.

Briefly referring now to FIG. 4, an illustration 400 of the load sensing unit 170 is shown for assessing and reporting load forces in an anatomical joint in accordance with an exemplary embodiment. The illustration shows the device 170 measuring a force, pressure, or load applied by the muscular-skeletal system, more specifically, the knee joint. It can report a load on each component and a balance of a medial condyle forces and a lateral condyle forces on the tibial plateau. The load is generally naturally balanced to provide even wear of the tibial surface, or a tibail prosthetic tray when included with a knee replacement surgery. The level and location of wear may vary based on a person's health and bone strength; hence, the need for the detection of force, location and balance. The load balance also contributes to the anatomical alignment (e.g., mechanical axis) and how this alignment is maintained.

In the illustration, device 170 collects load data for real-time viewing of the load forces over various applied loads and angles of flexion (when the knee is bent) or extension (when the knee is straight). As one example, it can convert an applied pressure associated with a force load on the anatomical joint into an electric signal via mechanical sensor, polymer sensor, strain gauge, piezoelectric transduction, ultrasonic waveguide displacement, or other transduction means. The sensing insert device 170 measures the level and distribution of load at various points on the prosthetic components (412/422) and transmits the measured load data by way data communication to the remote system 104 (or receiver station) for permitting visualization. This can aid the surgeon in providing soft tissue release (where ligaments may be titrated) or other adjustments needed to achieve optimal joint balancing.

Load sensing unit 170 has a contacting surface that couples to the muscular-skeletal system. As shown, a first and a second contacting surface respectively couple to a femoral prosthetic component 412 and a tibial prosthetic tray component 422. Device 170 is designed to be used in the normal flow of an orthopedic surgical procedure without special procedures, equipment, or components. One example of a load sensor unit is disclosed U.S. patent application Ser. No. 12/825,638 entitled "System and Method for Orthopedic Load Sensing Insert Device" filed Jun. 29, 2010 the entire contents of which are hereby incorporated by reference. Typically, one or more natural components of the muscular-skeletal system are replaced when joint functionality substantially reduces a patient quality of life. A joint replacement is a common procedure in later life because it is prone to wear over time, can be damaged during physical activity, or by accident.

A joint of the muscular-skeletal system provides movement of bones in relation to one another that can comprise angular and rotational motion. The joint can be subjected to loading and torque throughout the range of motion. The joint typically comprises two bones that move in relation to one another with a low friction flexible connective tissue such as cartilage between the bones. The joint also generates a natural lubricant that works in conjunction with the cartilage to aid in ease of movement. Load sensing unit 170 mimics the natural structure between the bones of the joint. Load sensing unit 170 has one or more articular surfaces on which a bone (femur 410) or a prosthetic component (412) can moveably couple. A knee joint is disclosed for illustrative purposes but load sensing unit 170 is applicable to other joints of the muscular-skeletal system. For example, the hip, spine, and shoulder have similar structures comprising two or more bones that move in relation to one another. In general, load sensing unit 170 can be used between two or more bones (or prosthetic components) allowing movement of the bones during measurement or maintaining the bones in a fixed position.

Returning back to FIG. 3 and further supporting step 314, an energy and range of a projected ultrasonic sensing field can be adjusted based on proximity of the components of the navigation device, and also at times, proximity and position of the load sensing unit 170. In the later, the navigation device 180 identifies the location of the load sensing unit 170 and ensures it is properly positioned for assessing alignment. This permits for controlled measurement of an alignment corresponding with a load balance of the applied anatomical force. It calculates the relationship of the forces on each compartment (e.g., condyles) with the varus and valgus alignment conditions. The adjusting is performed by the navigation device 180 previously shown in FIG. 1 and can adjust an ultrasonic waveform transmit sensitivity in accordance with a movement and proximity of the wand 200 to the receiver 220, for example, to match, compensate or characterize transmitter characteristics with the sound field environment (e.g., noise, airflow, temperature, etc.).

As an example, the receiver 220 signals the wand 200 to transmit ultrasonic waves at a higher energy level and repetition rate as a function of the distance there between. This can improve averaging and continuous tracking performance. It can also modify the transmitted wave shape depending on the distance or as a function of the detected environmental parameters. The shaping can occur at the processor on the receiver 220 (or pre-stored as a waveform in memory) responsive to an index flag, and the digital waveform is then communicated to the wand 200 which then transmits the pulse in accordance with the wave shape. Alternatively, the wand 200 can include a local memory to store wave shapes, and the receiver 220 transmits an index to identify which stored waveshape the wand 200 should transmit. One means of mapping a three-dimensional sensory field with the navigation device 180 is disclosed in U.S. Pat. No. 7,788,607 and patent application Ser. No. 12/853,987 entitled "Method and System for Mapping Virtual Coordinates" filed Dec. 1, 2006 the entire contents of which are hereby incorporated by reference.

The wand 200 can provide additional user interface control via a soft key 218. The receiver 220 can precisely track the wand 200 up to 2 m distances and report its position (among other parameters) on the GUI 108. It can track multiple wand locations if more than one wand is present, for example, to report positional information or movement of multiple points or objects. Although the receiver 220 is shown as stationary and the wand 200 as free to move, the reverse is true; the receiver 220 can track its own movement relative to a stationary wand 200 or a plurality of wands. U.S. Pat. No. 7,834,850 and patent application Ser. No. 12/900,662 entitled "Navigation Device Providing Sensory Feedback" filed Oct. 8, 2010 disclose principles of operation employed herein; the entire contents of which are hereby incorporated by reference. The receiver can calculate an orientation of the wand at the wand tip of the wand (4 cm or more away from any one of the plurality of ultrasonic transmitters) with respect to a virtual coordinate system of the receiver; and wirelessly transmit the alignment information with respect to three or more registered points in the ultrasonic sensing field in the virtual coordinate system of the receiver via a wireless radio frequency communication link.

FIG. 5A depicts an exemplary embodiment of the navigation system 500 for use as an alignment tool in total knee replacement procedures. The navigation system 500 includes the receiver 220, a mounting wand 230 and the wand 200; components of the navigation device 180 from FIG. 1. The wand 200 can be held in the hand for registering points and also be coupled to a guide or jig 520 as shown. This permits for navigating the guide or jig in view of the registered points. The guide jig supports the cutting of bones in relation to the mechanical axis of the joint for mounting prosthetic components thereto. It also includes the remote system 104 (e.g., laptop, mobile device, etc.) for presenting the graphical user interface (GUI) 108. The GUI 108 allows the user to visualize a navigated workflow and can be customized to the orthopedic procedure. The navigation system 500 as illustrated also includes the load sensing unit 170, shown inserted between the femur and tibia of the knee joint, and the earpiece 190 which receives from the remote system 104 audible messages related to the work flow GUI 108.

The system 500 assesses and reports in real-time the position of these points, or other registered points, by way of the GUI 108 on the remote system 108. It provides visual and auditory feedback related to cutting jig orientation and alignment, such as audible acknowledgements, haptic sensation (e.g., vibration, temperature), and graphical feedback (e.g., color, measurements, numbers, etc). Another example of an alignment tool used in conjunction with the embodiments herein contemplated is disclosed in U.S. Patent Application 61/498,647 entitled "Orthopedic Check and Balance System" filed Jun. 20, 2011 the entire contents of which are hereby incorporated by reference.

Returning back to FIG. 3 and further supporting step 316, the alignment and the load balance is reported at specific work flow times responsive to one or more steps during the work flow, for example, those associated with registering three-dimensional points in the ultrasonic sensing field. The steps associated therewith can include requiring the surgeon to identify an anatomical landmark, for example, by pressing the wand button, tracing out a contour of a bone or identifying points on a guide or jig, or navigating a guide into a predetermined orientation (position, location, angle, etc.). Other steps can include femur head identification, the use of a different cutting jig (femur, tibia, 4in1 block rotation, etc.) requiring detachment and reattachment of the wand 200, controlling the user interface 108 (e.g., pagination, markers, entries, etc.), assessing/performing bone cuts, assessing/performing soft tissue release, insertion/repositioning/removal of the load sensing unit 170 or navigation device 180 components or other commonly practiced work flow steps.

One exemplary embodiment of providing sensory feedback in a navigated workflow with the sensorized tools is disclosed in U.S. patent application Ser. No. 12/900,878 filed Oct. 8, 2010 entitled "Navigation System and User Interface For Directing a Control Action", the entire contents of which are hereby incorporated by reference.

Briefly referring again to FIG. 5, the receiver 220 precisely tracks both wands 200-230 and reports their position on the GUI 108 as part of the navigated workflow procedure. During the procedure, the receiver 220 is rigidly affixed to the femur bone for establishing a base (or virtual) coordinate system. The mounting wand 230 is rigidly affixed to the tibia for establishing a second coordinate system with respect to the base coordinate system. The wand 200 is used to register points of interest with the receiver 220. The points of interest can be on a bone or on cutting jigs 520 used during surgery. Thereafter, the wand 200 can be rigidly coupled to the cutting jig 520 (femur/tibia) to establish virtual cut angles for making corresponding cuts on the bones. The navigation system 500 reports real-time alignment of the cutting jigs 520 and bones by way of direct communication between the wands 220-230 and the receiver 220; no computer workstation is required there between.

In one arrangement, the wand emits a plurality of ultrasonic pulses from a plurality of ultrasonic transmitters configured to transmit the ultrasonic pulses. The receiver with a plurality of microphones captures the ultrasonic pulses and digitally samples and stores a history of received ultrasonic waveforms in memory. It estimates from the stored ultrasonic waveforms a time of flight between transmitting and receiving of the ultrasonic pulses, and identifies a location of the wand from the time of flight measurements received at the plurality of microphones. It then calculates for the plurality of ultrasonic waveforms stored in the memory a phase differential between the ultrasonic waveforms and previously received ultrasonic waveforms, and updates the location of the wand from a mathematical weighting of the time of flight with the phase differential.

In addition to visual and auditory feedback provided by the GUI 108 on the laptop 104, the load balance and alignment information can be audibly presented via the earpiece 190 responsive to completion of the one or more steps during the work flow as recited in step 318 in the description of method 300 of FIG. 3. The earpiece 190 may receive such audio content directly from the laptop 104 or the receiver 220, which is also equipped with wireless communication (e.g, Bluetooth). The receiver 220 and laptop 104 can provide Bluetooth profiles such as Human Interface Device Profile (HID), Headset Profile (HSP), Hands-Free Profile (HFP) or Serial Port Profile (SPP) for low complexity overhead, though is not limited to these. The Bluetooth profile provides a wireless interface specification for Bluetooth-based communication between devices.

As another example, audio feedback can be provided for any of these steps or other steps associated with assessing both balance and alignment, for instance, audibly indicating the force level, for instance, by increasing a media loudness (e.g. tone, beep, synthetic message) or frequency corresponding to the level while evaluating alignment. As another example, the earpiece 190 can provide synthetic voice messages for a "to do" step in the work flow of the GUI 108. It can also be configured to chime or respond to a predetermined parameter, for example, when ideal balance and alignment has been achieved.

This information can also be visually reported via the GUI 108 previously shown in the navigation system 500 of FIG. 5A. That is, the alignment and balance information be numerically shown with other graphical features (e.g., color, size, etc.) for emphasis. One benefit of audible feedback is that it permits the surgeon to look and listen separately to alignment and balance. For instance, the GUI can provide visual alignment information while the earpiece provides audio level for force. In situations where two earpieces are used, the force balance may be applied as pan balance between earpieces. Balance can be noted when the sound parameters (e.g., loudness, tone, etc.) from the left and right earpiece are equal. The visual and auditory combination can assist the surgeon in comprehending load balance and alignment during surgery.

Figure 5B:
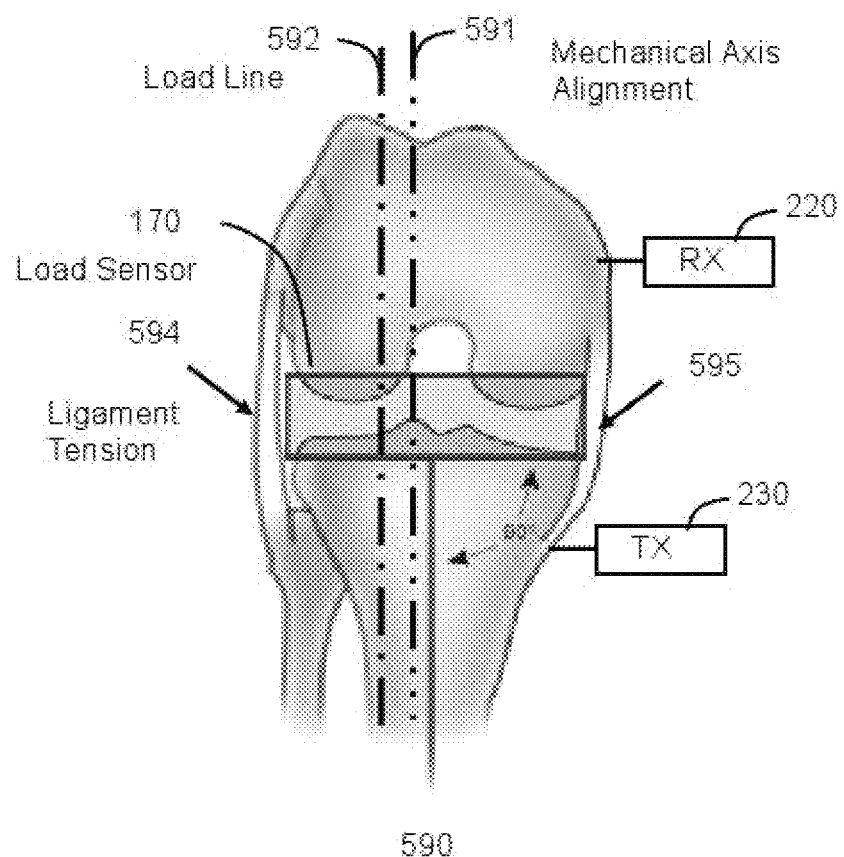
FIG. 5B illustrates an integrated alignment and balance Graphical User Interface (GUI) in accordance with one embodiment.

FIG. 5B illustrates an integrated visual information GUI 590 for efficiently displaying balance in view of alignment, for instance, to show the mechanical axis 591 and the load line 592 overlay with reference to anatomical load forces. It provides visual feedback and audible information over the earpiece. Briefly, the Receiver 220 and Wand (TX) 230 render of the mechanical axis 591; that is, the alignment between bone coordinate systems. The load sensor 170 data provides the GUI rendering of the load line 592; that is, the location and loading of the forces on the knee compartments that contribute to the overall stability of the prosthetic knee components. The overlay GUI 590 can also simulate soft tissue anatomical stresses associated with the alignment and balance information. For example, the GUI 590 can adjust a size and color of a graphical ligament object corresponding to a soft tissue ligaments according to the reported alignment and balance information. The ligament object 594 can be emphasized red in size to show excess tension or stress as one example. Alternatively, ligament object 595 can be displayed neutral green if the knee compartment forces for alignment and balance result within an expected, or acceptable, range, as another example. Such predictive measurements of stress based on alignment and balance data can be obtained, or predetermined, from widespread clinical studies or from measurements made previously on the patient's knee, for example, during a clinical, or pre-op.

Figure 6:
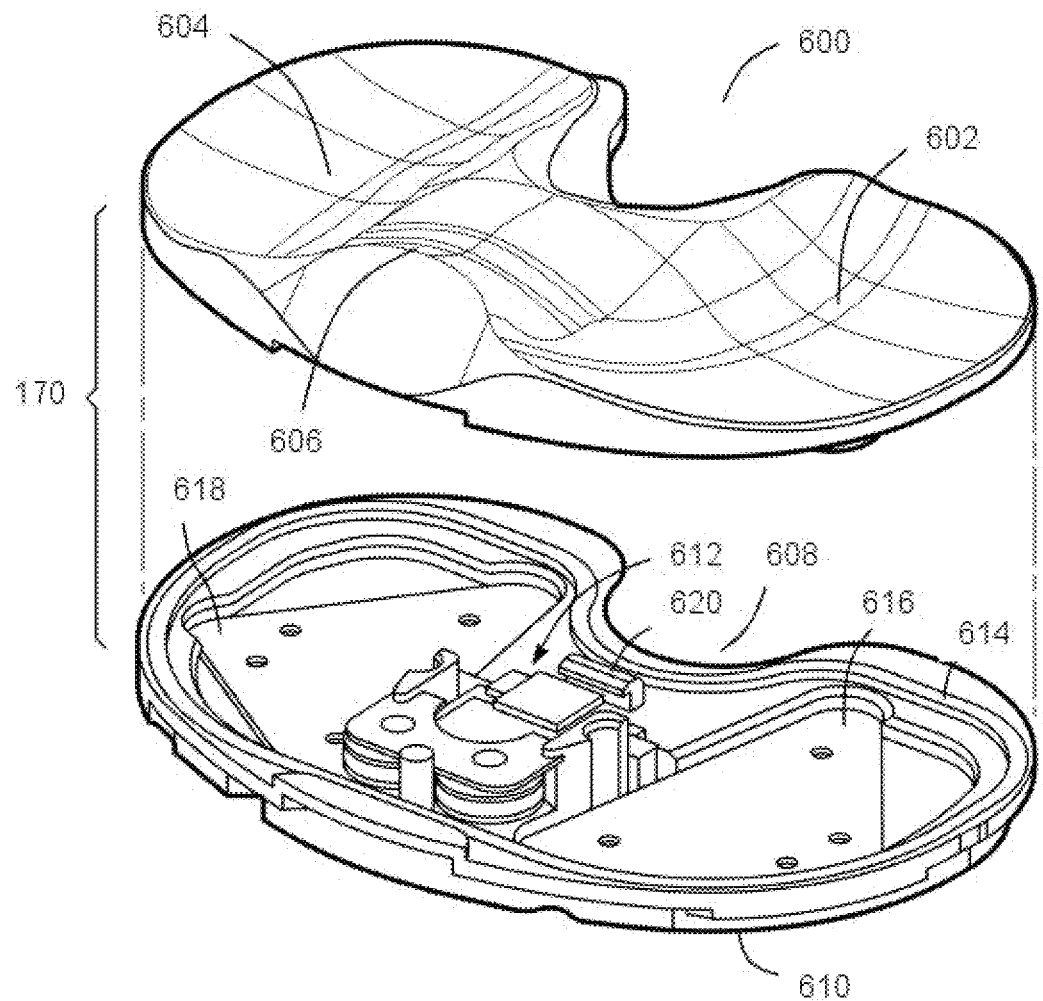
FIG. 6 illustrates a load sensing unit for measuring a parameter of the muscular-skeletal system in accordance with an example embodiment.

FIG. 6 illustrates the load sensing unit 170 for measuring a parameter of the muscular-skeletal system in accordance with an example embodiment. In general, and with respect to FIG. 4, it is the insert component 170 between the femur prosthetic component 412 and the tibia prosthetic component 422 which together comprises a joint replacement system to allow articulation. In the example, load sensing unit 170 is a prosthetic insert that is a wear component of a knee joint replacement system. The prosthetic insert has one or more articular surfaces (602/604) that allow joint articulation. As shown, load sensing unit 170 has two articular surfaces 602 and 604 with underlying sensors for measuring load. The articular surface is low friction and can absorb loading that occurs naturally based on situation or position. The contact area between surfaces of the articulating joint can vary over the range of motion. The articular surface of a permanent insert will wear over time due to friction produced by the prosthetic component surface contacting the articular surface during movement of the joint. Ligaments, muscle, and tendon hold the joint together and motivate the joint throughout the range of motion.

Load sensing unit 170 is an active device having a power source, electronic circuitry, transmit capability, and sensors within the body of the prosthetic component. As disclosed herein, load sensing unit 170 can be used intra-operatively to measure parameters of the muscular-skeletal system to aid in the installation of one or more prosthetic components. As shown, operation of load sensing unit 170 is shown as a knee insert to illustrate operation and measurement of a parameter such as loading and balance. Load sensing unit 170 can be adapted for use in other prosthetic joints having articular surfaces such as the hip, spine, shoulder, ankle, and others. Alternatively, load sensing unit 170 can be a permanent active device that can be used to take parameter measurements over the life of the implant. One example of the wireless load sensor unit is disclosed U.S. patent application Ser. No. 12/825,724 entitled "Wireless Sensing Module for Sensing a Parameter of the Muscular-Skeletal System" filed Jun. 29, 2010 the entire contents of which are hereby incorporated by reference.

In both a trial, or permanent insert, load sensing unit 170 is substantially equal in dimensions to a passive final prosthetic insert. In general, the substantially equal dimensions correspond to size and shape that allow the insert to fit substantially equal to the passive final prosthetic insert. In the intra-operative example, the measured loading and balance using load sensing unit 170 as a trial insert would be substantially equal to the loading and balance seen by the final insert. It should be noted that load sensing unit 170 for intra-operative measurement could be dissimilar in shape or have missing features that do not benefit the trial during operation. The insert is positionally stable throughout the range of motion equal to that of the final insert. The exterior structure of load sensing unit 170 is formed from at least two components.

In the embodiment shown, load sensing unit 170 comprises a support structure 600 and a support structure 608. Support structures 600 and 608 have major support surfaces that are loaded by the muscular-skeletal system. As previously mentioned, load sensing unit 170 is shown as a knee insert to illustrate general concepts and is not limited to this configuration. Support structure 600 has an articular surface 602 and an articular surface 604. Condyles of a femoral prosthetic component articulate with surfaces 602 and 604. Loading on the prosthetic knee joint is distributed over a contact area of the articular surfaces 602 and 604. In general, accelerated wear occurs if the contact area is insufficient to support the load. A region 606 of the support structure 600 is unloaded or is lightly loaded over the range of motion. Region 606 is between the articular surfaces 602 and 604. It should be noted that there is an optimal area of contact on the articular surfaces to minimize wear while maintaining joint performance. The contact location can vary depending on the position within the range of motion of the muscular-skeletal system. Problems may occur if the contact area falls outside a predetermined area range within articular surfaces 602 and 604 over the range of motion.

In one embodiment, the location where the load is applied on articular surfaces 602 and 604 can be determined by the sensing system. This is beneficial because the surgeon now has quantitative information where the loading is applied. The surgeon can then make adjustments that move the location of the applied load within the predetermined area using real-time feedback from the sensing system to track the result of each correction. The support structure 608 includes sensors and electronic circuitry 612 to measure loading on each articular surface of the insert. A load plate 616 underlies articular surface 602. Similarly, a load plate 618 underlies articular surface 604. Force, pressure, or load sensors (not shown) underlie load plates 616 and 618. In one embodiment, load plates 616 and 618 distribute the load to a plurality of sensors for determining a location where the load is applied. In the example, three sensors such as a piezo-resistive sensor underlies a corresponding load plate. The sensors are located at each vertex of the triangular shaped load plate.

Although the surface of load plates 616 and 618 as illustrated, are planar they can be conformal to the shape of an articular surface. A force, pressure, or load applied to articular surfaces 602 and 604 is respectively coupled to plates 616 and 618. Electronic circuitry 612 is operatively coupled to the sensors underlying load plates 616 and 618. Plates 616 and 618 distribute and couple a force, pressure, or load applied to the articular surface to the underlying sensors. The sensors output signals corresponding to the force, pressure, or load applied to the articular surfaces, which are received and translated by electronic circuitry 612. The measurement data can be processed and transmitted to a receiver external to load sensing unit 170 for display and analysis. In one embodiment, the physical location of electronic circuitry 612 is located between articular surfaces 602 and 604, which correspond to region 606 of support structure 600. A cavity for housing the electronic circuitry 112 underlies region 606. Support structure 608 has a surface within the cavity having retaining features extending therefrom to locate and retain electronic circuitry 612 within the cavity. The retaining features are disclosed in more detail hereinbelow. This location is an unloaded or a lightly loaded region of the insert thereby reducing a potential of damaging the electronic circuitry 612 due to a compressive force during surgery or as the joint is used by the patient. In one embodiment, a temporary power source such as a battery, capacitor, inductor, or other storage medium is located within the insert to power the sensors and electronic circuitry 612.

Support structure 600 attaches to support structure 608 to form the insert casing. Internal surfaces of support structures 600 and 608 mate together. Moreover, the internal surfaces of support structures 600 and 608 can have cavities or extrusions to house and retain components of the sensing system. Externally, support structures 600 and 608 provide load bearing and articular surfaces that interface to the other prosthetic components of the joint. The support structure 608 has a support surface 610 that couples to a tibial implant. In general, the support surface 610 has a much greater load distributing surface area that reduces the force, pressure, or load per unit area than the articulating contact region of articular surfaces 602 and 604.

The support structures 600 and 608 can be temporarily or permanently coupled, attached, or fastened together. As shown, load sensing unit 170 can be taken apart to separate support structures 600 and 608. A seal 614 is peripherally located on an interior surface of support structure 608. In one embodiment, the seal is an o-ring that comprises a compliant and compressible material. The seal 614 compresses and forms a seal against the interior surface of support structures 600 and 608 when attached together. Support structures 600 and 608 form a housing whereby the cavities or recesses within a boundary of seal 614 are isolated from an external environment. In one embodiment, a fastening element 620 illustrates an attaching mechanism. Fastening element 620 has a lip that couples to a corresponding fastening element on support structure 600. Fastening element 620 can have a canted surface to motivate coupling. Support structures 600 and 608 are fastened together when seal 614 is compressed sufficiently that the fastening elements interlock together. Support structures 600 and 608 are held together by fastening elements under force or pressure provided by seal 614 or other means such as a spring. Not shown are similar fastening elements that may be placed in different locations to secure support structures 600 and 608 equally around the perimeter if required.

In one embodiment, support structure 600 comprises material commonly used for passive inserts. For example, ultra high molecular weight polyethylene can be used. The material can be molded, formed, or machined to provide the appropriate support and articular surface thickness for a final insert. Alternatively, support structures 600 and 608 can be made of metal, plastic, or polymer material of sufficient strength for a trial application. In an intra-operative example, support structures 600 and 608 can be formed of polycarbonate. It should be noted that the long-term wear of the articular surfaces is a lesser issue for the short duration of the joint installation. The joint moves similarly to a final insert when moved throughout the range of motion with a polycarbonate articular surface. Support structure 600 can be a formed as a composite where a bearing material such as ultra high molecular weight polyethylene is part of the composite material that allows the sensing system to be used both intra-operatively and as a final insert.

Figure 7:
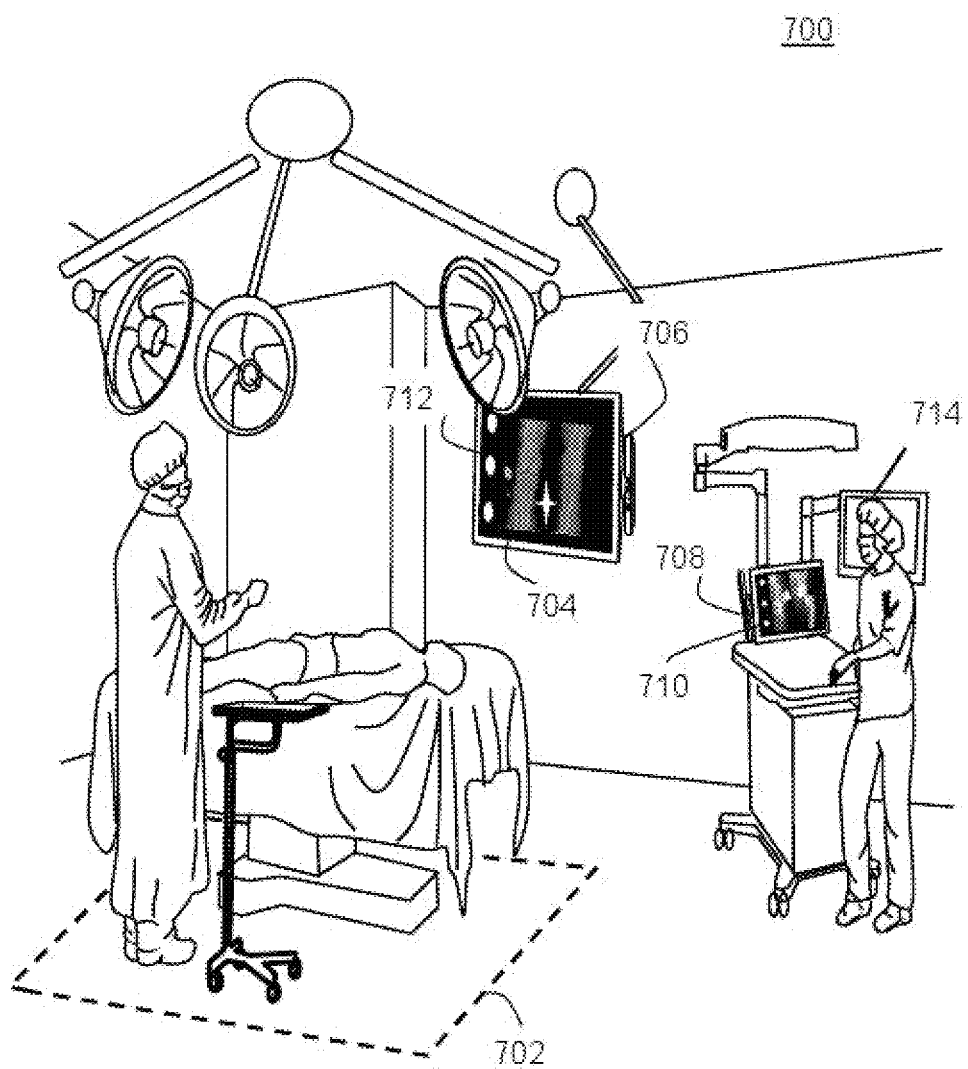
FIG. 7 illustrates one or more remote systems in an operating room in accordance with an example of FIG. 8 to illustrate the detector detecting one of visual, motion, or audio queue from a user in accordance with an example embodiment.

FIG. 7 illustrates one or more remote systems in an operating room in accordance with an example embodiment. In general, an operating room includes a region where access is limited. Typically, personnel and equipment required for the procedure stay within a sterile field 702. Sterile field 702 is also known as a surgical field. Filtered air flows through sterile field 702 to maintain the region free of contaminants. The airflow can be laminar through sterile field 702 to carry contaminants away from the procedure thereby maintaining the sterile environment.

Remote systems as herein include a processor, communication circuitry, and a display. The communication circuitry couples to one or more devices for receiving measurement data. The processor can process the data to support a work-flow of the procedure. Processing of the data can include audio, visual, and haptic feedback in real-time that allows rapid assessment of the information. In general, the measured quantitative data can be displayed on a display that is in the line of sight of the user but may not be in the sterile field. In a first example, a remote system 712 is attached to a ceiling. A mechanical arm extends from the ceiling that allows remote system 712 to be moved to an appropriate height and angle for viewing within the sterile field. Remote system 712 includes a display 704 and a detector 706. In a second example, a remote system 714 is on a portable platform that can be wheeled to an appropriate location. Remote system 714 includes a display 710 and a detector 706. One example of such a remote system is disclosed in U.S. patent application Ser. No. 12/723,486 entitled "Sterile Networked Interface for Medical Systems" filed Mar. 12, 2010 the entire contents of which are hereby incorporated by reference.

Remote systems 712 and 714 operate in a similar fashion. The remote system 712 may be used for illustrative purposes but each example also applies to portable remote system 714 and the corresponding components thereof. Although not shown, a tool, equipment, or device is used to measure a parameter of the muscular-skeletal system within surgical field 702. For example, a load sensing unit inserted in a prosthetic knee joint wirelessly sends data to remote system 712. A navigation system can provide position and alignment information of the joint installation. A visualization of the prosthetic knee joint can be displayed on display 704 with the quantitative measurements related to load and alignment. The load sensing unit can provide quantitative measurements of the load magnitude and balance between condyles. The navigation system can provide information on alignment relative to the mechanical axis of the leg. Furthermore, position data of the femur in relation to the tibia can also be shown on remote system 712. The quantitative measurement information displayed on remote system 712 can be used select prosthetic components and effect changes before final components are installed.

The surgeon and other personnel within sterile field 702 can view display 704. The detector 706 of remote system 712 and similarly detector 708 of remote system 714 includes multiple sensors that are directed towards sterile field 702. Sensors included in detector 706 can be but not limited to visual, audio, and motion sensors. The sensors can be used to control the GUI on remote system remotely. For example, gestures can be received by detector 706 and identified that results in an action. Similarly, audible commands can be recognized that results in an action. The gestures can control the work-flow, how data is presented, image size, a region of the screen, and access other programs to name but a few commands. Detector 706 provides a means of controlling remote system 712 from a distance. Detector 706 can be used to modify or change a device used in a procedure. For example, device, equipment, or tool settings could be adjusted using gestures or audible commands that might otherwise be difficult during the procedure.

Detector 706 couples to the processor and display of remote system 712. Feedback can be provided by the system in response to the action received by detector 706 from the user. The response can be visual, audio, haptic, or other means that is readily detected by the user. The response can be provided by detector 706, display 704, or other devices. Similarly, visual, audio, or haptic feedback can be provided by detector 706 or display 704 based on the quantitative data received from equipment, instruments, or tools being used to assess the muscular-skeletal system of the patient for the prosthetic joint implant. At this time, orthopedic surgeons rely on subjective feel with little or no quantitative measurement information related to combined alignment, position, loading, and load balance. Remote systems 712 and 714 are hands free operating room systems that allows the surgeon to receive quantitative data in a non-obtrusive manner that supports an optimal installation while reducing surgical time for the patient. The quantitative data from each surgery can be data logged with the corresponding work-flow step of the procedure for review and analysis as it relates to both short and long term outcomes.

Figure 8A:
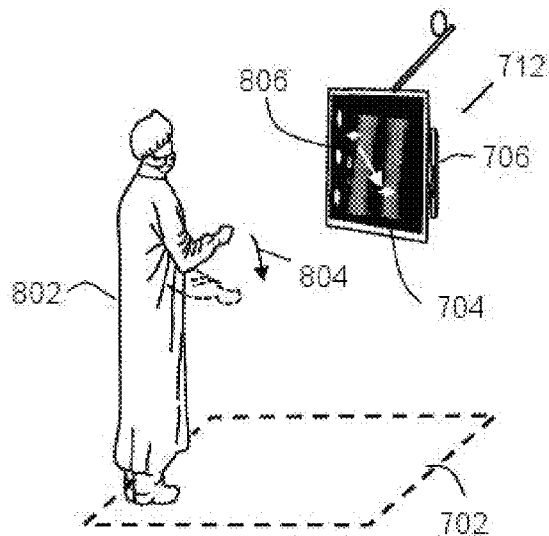
FIG. 8A illustrates the detector detecting one of visual, motion, or audio queue from a user in accordance with an example embodiment.

FIG. 8A illustrates detector 706 detecting one of visual, motion, or audio queue from a user 802. User 802 resides in sterile field 702 of an operating room. Instruments, personnel, and the patient have been removed for clarity of the user operation. Detector 706 detects a gesture 804 or motion used in the operation of the GUI of display 704. Motion detection or visual input from detector 706 is analyzed to recognize the command. In the example, user 802 wants to focus in on a different area of the screen. Gesture 804 is recognized and an action is taken. The example action as shown causes the screen to translate to the area directed by user 802. In one embodiment, the system can provide feedback to the command recognition before the action is taken. Display 704 or detector 706 can provide visual, audible, or haptic feedback to indicate recognition of the command. In some circumstances, remote system 712 may await a visual or audible confirmation to initiate the action. Although shown with gestures, the command could be given audibly or by the parameter measurement instrument used in the orthopedic procedure coupled to.

Figure 8B:
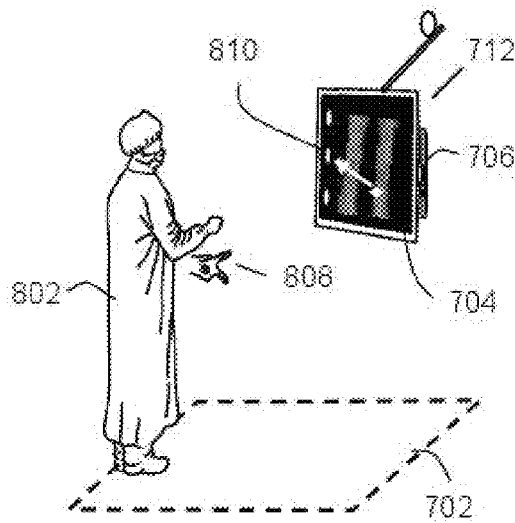
FIG. 8B illustrates the detector detecting one of visual, motion, or audio queue from a user in accordance with an example embodiment.

FIG. 8B illustrates detector 706 detecting one of visual, motion, or audio queue from a user 802. User 802 is providing a gesture 808 that moves display 704 back to the previous screen. Detector 706 receives the visual or motion queue. The visual or motion queue is recognized resulting in an action to move back to the previous screen. In the example, remote system 704 can be coupled to the surgical navigation device and the load sensing unit. Quantitative measurement data on position, alignment, load, and load balance is provided on display 704. As mentioned previously, remote system 712 can be a computer system having one or more processors and digital signal processors for analyzing the quantitative data and the visual, motion, and audio queues from detector 706. Alternatively, detector 706 can have internal processors for analyzing detector input for recognition of commands and the resultant action. In general, a small set of gestures that can control and allow interaction with the GUI on display 704 would result in better outcomes as quantitative data can be added to subjective feel in a manner that adds little or no time to how orthopedic surgeries are currently being performed.

Figure 8C:
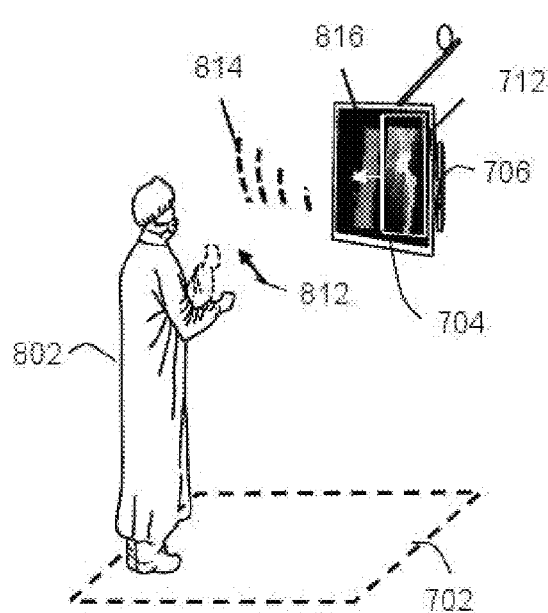
FIG. 8C illustrates the detector detecting one of visual, motion, or audio queue from a user in accordance with an example embodiment.

FIG. 8C illustrates detector 706 detecting one of visual, motion, or audio queue from a user 802. User 802 is shown providing a gesture 812 that is detected by detector 706. Detector 706 recognizes gesture 812 and responds by performing an action corresponding to gesture 812. In the example, a step of the work-flow has been completed and gesture 812 results in the action that the remote system displays the next page of the work-flow. The new page of the work-flow may require different parameter measurements to be performed at different joint positions. The remote system 712 can respond by visual, audible, haptic, or other means. In one embodiment, remote system 712 can respond to gesture 812 with an audible output 814. Audible output 814 can acknowledge the detection of gesture 812 and the action taken thereof. Audible output 814 can further describe the action being taken to ensure the correct action is being taken. Alternatively, the action can be indicated on screen 704. Audible output 814 can also be produced in response to measurement data output by the orthopedic measurement devices (not shown) coupled to remote system 712. For example, quantitative measured data related to alignment to the mechanical axis can be analyzed by remote system 712. An audible output 814 can be provided indicated that it is more than a predetermined range. Further audible output can be provided related to the amount of valgus or vargus misalignment. User 802 could continue work on the patient getting real-time audio feedback on the measurements as it pertains to the steps of the work-flow. Similarly, audible output 814 can be provided when the load sensing unit is placed in the muscular-skeletal system. The audible output 814 can recite load magnitude and load balance on the load sensing unit. Audible output 814 can be non-verbal such as tone or sound magnitude changes for audibly indicating measured parameters. Audible output 814 can be directed to an earpiece worn by user 802 as disclosed above. A further benefit can be achieved in providing audible direction of work-flow steps that incorporates combined data from the navigation system and the load sensing unit into a surgical related format that user 802 can perform on the patient or prosthetic components.

Figure 8D:
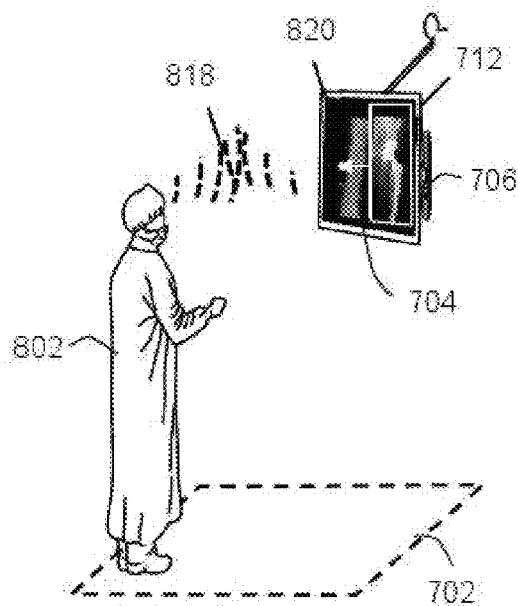
FIG. 8D illustrates the detector detecting one of visual, motion, or audio queue from a user in accordance with an example embodiment.

FIG. 8D illustrates detector 706 detecting one of visual, motion, or audio queue from a user 802. User 802 can provide an audible command that is detected by detector 706. Detector 706 or system 712 can have voice recognition software for assessing the audible command. Detector 706 upon recognizing audible command 813 initiates an action as described herein. Audible commands 818 can be used to control the GUI on display 704 or provide feedback in response to a visual or audible queue provided by remote system 712. Audible command 818 can also be used to change settings of instruments, equipment or tools coupled to remote system 712.

Figures 9A, 9B:
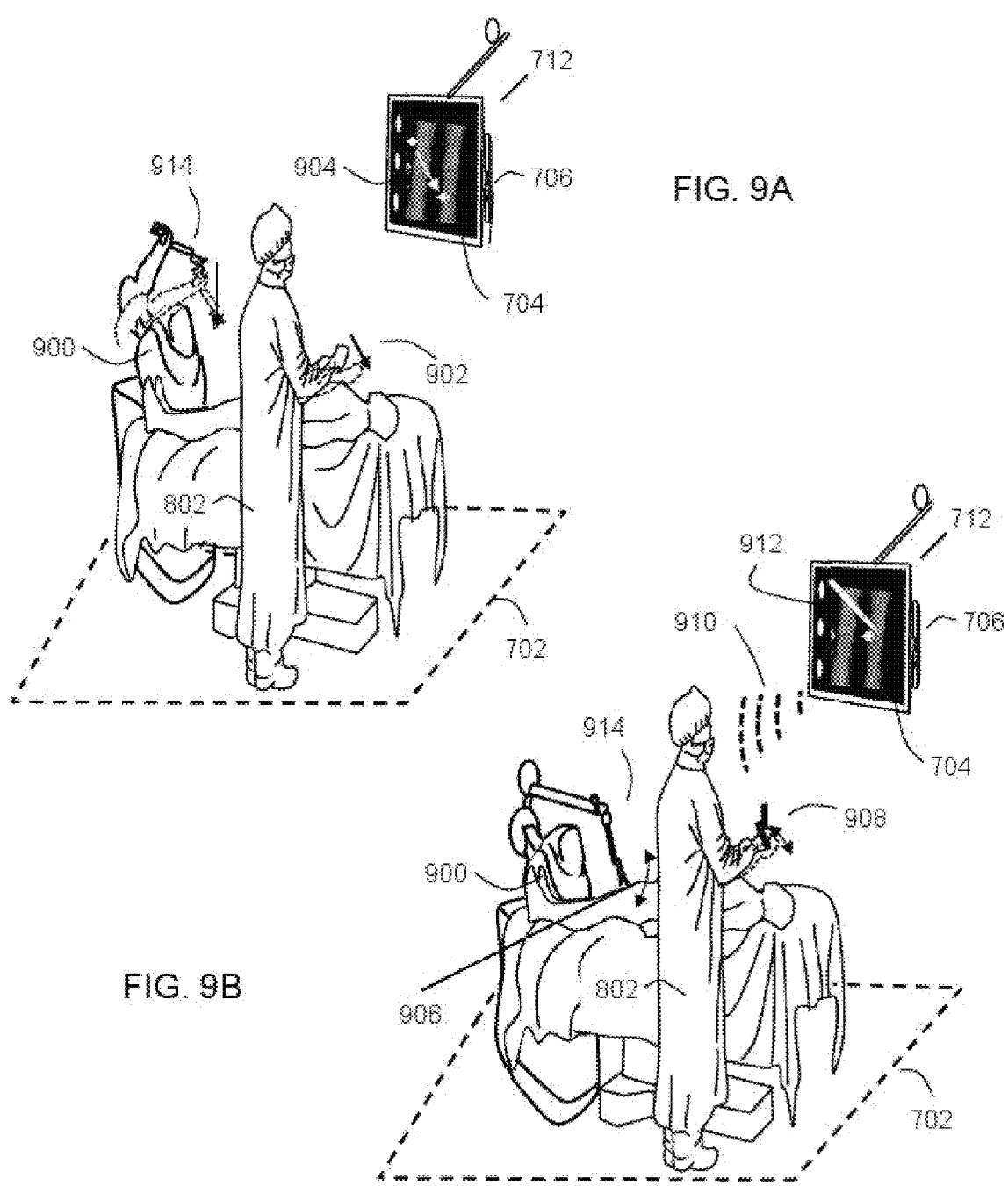
FIG. 9 illustrates a robotic tool coupled to the remote system in accordance with an example embodiment.

FIG. 9 illustrates a robotic tool 900 coupled to remote system 712 in accordance with an example embodiment. In one embodiment, robotic tool 900 includes an arm 914 for supporting operations such as bone modifications and cuts for accepting prosthetic components. Robotic tool 900, the load sensing unit, and the navigation system couple to remote system 712. Robotic tool 900 utilizes image data with actual points on the patient muscular-skeletal system to map a region of interest. Arm 914 of robotic tool 900 is motorized to precisely move in 3D space in relation to the mapped region. Instruments and tools can be attached to arm 914. For example, a cutting device can be attached to arm 914 where the location in 3D space of the leading edge of the cutting device is known and controlled by robotic tool 900. Robotic tool 900 can aid user 802 in making precise and specific muscular-skeletal modifications. In the example, robotic tool 900 can be programmed to cut bone regions to receive one or more prosthetic components. Robotic tool 900 can be used in conjunction with the navigation system and the load sensing unit. The user interface on display 704 supports the work-flow that includes robotic tool 900. In the example, quantitative data related to the position of arm 914 of robotic tool 900, loading, joint position, and alignment can be provided on display 704. A gesture 902 can be used to generate an action on robotic tool 900. Detector 706 detects and recognizes gesture 902 and generates an action. Remote system 712 can provide an audio output 910. In the example, audio output 910 can be a response to gesture 902. The audio output 910 can request confirmation to perform the action. User 802 can confirm by gesture 908 or audibly that the action is correct and to initiate the action. An example of the action is gesture 902 causing robotic arm 914 to move towards the surgical area. Detector 706 detects and recognizes the confirmation gesture 908 and initiates robotic arm movement.

Figure 10:
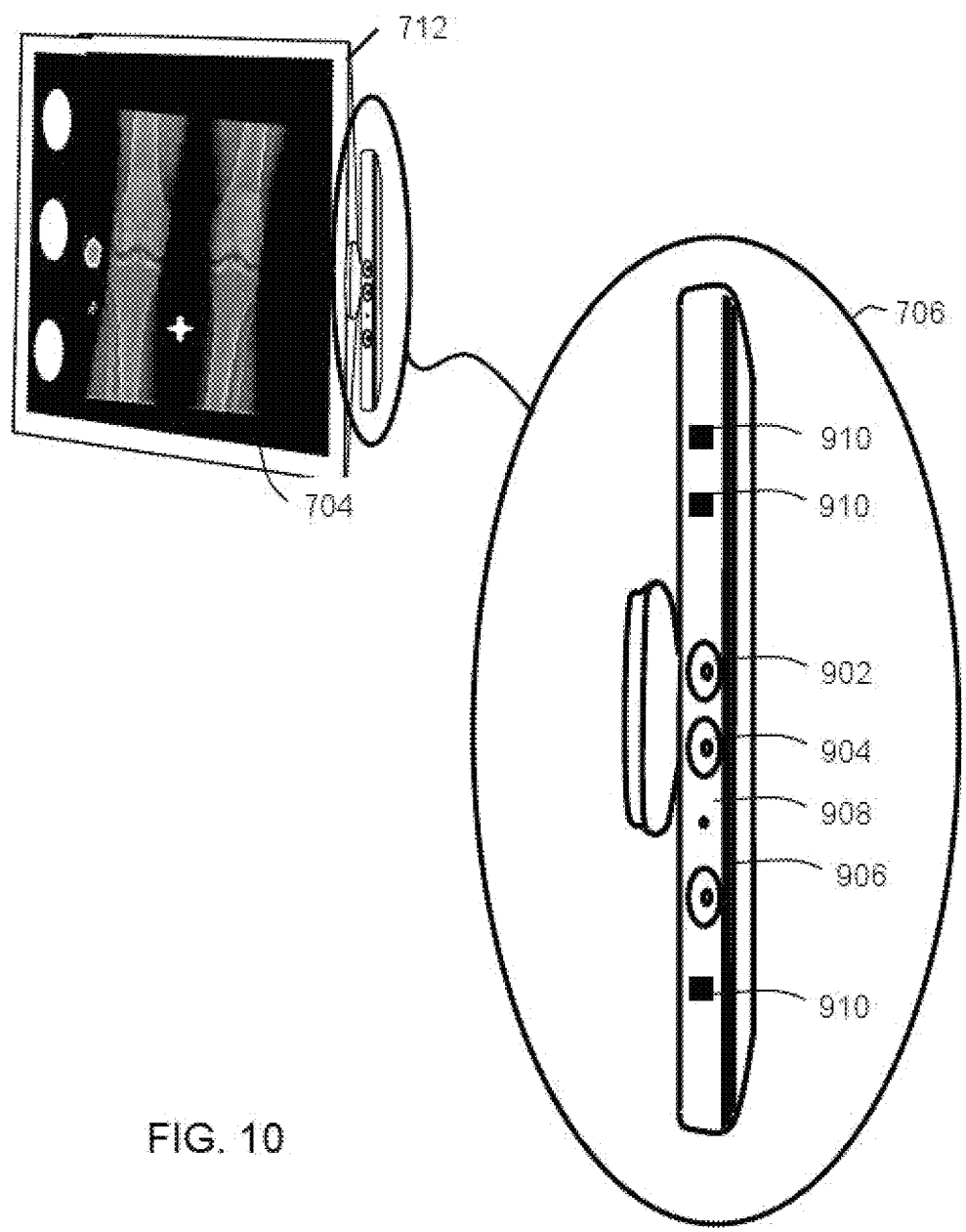
FIG. 10 illustrates a sensor array of detectors in accordance with an example embodiment.

FIG. 10 illustrates a sensor array of detector 706 in accordance with an example embodiment. Detector 706 has more than one sensor for visual, motion, and audio detection. In one example, detector 706 includes a camera 902 and one or more infrared sensors 904. Detector 706 can view the sterile field of the operating room scanning the space in 3D. Detector 706 can further include ultrasonic sensors 910. Ultrasonic sensors 910 can be used for motion detection within the sterile field. A sensor for distinguishing depth of image can further support 3D recognition. Detector 706 further includes one or more audio transducers 908. Transducers 908 can be a microphone for receiving audio and a speaker for providing an audio output. As mentioned previously, detector 706 can include one or more processors or digital signal processors for capturing changes in image and motion. The one or more processors can utilize software for analyzing captured motion, voice recognition, sound generation, and voice generation. Recognition software can be used to determine difference between normal physical activities within the sterile space from gestures. Similarly, the transducers 908 can be used to identify and localized source vocalization such as the surgeon. Motion and sound recognition supports remote system 712 placed outside the sterile field for allowing user control of the GUI. Moreover, remote system 712 can reduce staff required in the operating room thereby lowering exposure of contaminants to the patient. Remote system 712 further facilitates the integration of measured data on the muscular-skeletal system that can quantify a subjective feel of a surgeon. The measured data can be provided verbatim in real-time on display 704 of remote system 712. The quantitative measurements by itself may not be synthesized by the user rapidly nor may it be readily adapted to the task being performed in the work-flow. Remote system 712 can analyze the quantitative data and translate the measurements into an action to be taken by the user that is a step of the work-flow. For example, load and load balance measurements can be translated can be translated to specific soft tissue tensioning steps performed by the surgeon to reduce load and increase balance. Thus, remote system 712 can provide real-time feedback to measurement tools and the user respectively based on measurements and motion/audio detection that integrates well with existing surgical work-flows.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

These are but a few examples of embodiments and modifications that can be applied to the present disclosure without departing from the scope of the claims stated below. Accordingly, the reader is directed to the claims section for a fuller understanding of the breadth and scope of the present disclosure.

Where applicable, the present embodiments of the invention can be realized in hardware, software or a combination of hardware and software. Any kind of computer system or other apparatus adapted for carrying out the methods described herein are suitable. A typical combination of hardware and software can be a mobile communications device with a computer program that, when being loaded and executed, can control the mobile communications device such that it carries out the methods described herein. Portions of the present method and system may also be embedded in a computer program product, which comprises all the features enabling the implementation of the methods described herein and which when loaded in a computer system, is able to carry out these methods.

While the preferred embodiments of the invention have been illustrated and described, it will be clear that the embodiments of the invention are not so limited. Numerous

What is claimed, is:

1. A medical system for generating quantitative measurements on the muscular-skeletal system, comprising:
a load sensing device configured to couple to the muscular-skeletal system to measure a load magnitude and a position of load applied thereto;
an inertial sensing device configured to measure muscular-skeletal alignment; and
a remote system having a display configured to wirelessly couple to the inertial sensing device and the load sensing device wherein the remote system is configured to receive quantitative measurement data from the load sensing device and the inertial sensing device and where the remote system is configured to display load magnitude, position of load, and alignment data.

2. The system of claim 1, further comprising a detector unit coupled to the remote system for receiving visual, audio, or motion queues from within a surgical field.

3. The system of claim 1, wherein the inertial sensing device comprises a three-axis accelerometer.

4. The system of claim 1 wherein the inertial sensing device is configured to provide position measurement data and wherein the remote system comprises a processor, display, and software.

5. The system of claim 4 wherein the inertial sensing device is configured to measure 3 and 6 axis tilt during motion and while stationary.

6. The system of claim 1 wherein at least one of an ultrasonic transducer, MEMs microphone, electromagnets, optical elements, metallic objects or other transducers are configured to convert or convey a physical movement to an electrical signal and support measurement of muscular-skeletal alignment.

7. The system of claim 6 wherein a time of flight or a differential time of flight signal is configured to be measured by at least one of an ultrasonic transducer, MEMs microphone, electromagnets, optical elements, metallic objects or other transducers corresponding to muscular-skeletal alignment.

8. The system of claim 1 further including a detector unit coupled to the remote system for receiving visual, audio, or motion queues from within a surgical field where an action is generated upon receiving one of the visual, audio, or motion queues.

9. The system of claim 8, where the remote system comprises a computer system coupled to a display, where the display presents load magnitude, position of load, and alignment measurement data.

10. An operating room system comprising:
one or more sensors configured to measure load and position of load of a muscular-skeletal system;
an inertial sensing device configured to measure alignment of the muscular-skeletal system; and
a remote system having a display configured to wirelessly receive load, position of load, and alignment quantitative measurement data load where the remote system is configured to display load magnitude, position of load, and alignment data to support installation of at least one prosthetic component; and
a detector unit coupled to the remote system for receiving visual, audio, or motion queues from within a surgical field.

11. The system of claim 10 where an action is generated by the remote system in response to one of a visual, audio, or motion queue.

12. The system of claim 10 where the remote system displays load balance quantitative measurement data.

13. An operating room system configured to support a knee joint operation comprising at least one prosthetic component having sensors therein the operating room system the comprising:
one or more sensors configured to measure load and position of load of a knee joint;
at least one inertial sensing device configured to measure leg alignment; and
a remote system having a display configured to wirelessly couple to the one or more sensors configured to measure load and position of load and the inertial sensing device configured to measure leg alignment where the remote system is configured to receive quantitative measurement data and where the remote system is configured to display load magnitude, position of load, and alignment data.

14. The system of claim 13 further including a detector unit coupled to the remote system for receiving visual, audio, or motion queues from within a surgical field where an action is generated upon receiving one of the visual, audio, or motion queues.

15. The system of claim 13, wherein the inertial sensing device comprises a three-axis accelerometer.

16. The system of claim 13 wherein the inertial sensing device is configured to provide position measurement data and wherein the remote system comprises a processor, display, and software.

17. The system of claim 16 wherein the inertial sensing device is configured to measure 3 and 6 axis tilt during motion and while stationary.

18. The system of claim 13 wherein at least one of an ultrasonic transducer, MEMs microphone, electromagnets, optical elements, metallic objects or other transducers are configured to convert or convey a physical movement to an electrical signal and support measurement of muscular-skeletal alignment.

19. The system of claim 18 wherein a time of flight or a differential time of flight signal is configured to be measured by at least one of an ultrasonic transducer, MEMs microphone, electromagnets, optical elements, metallic objects or other transducers corresponding to muscular-skeletal alignment.

20. The system of claim 13 wherein the remote system displays load balance quantitative measurement data.

* * * * *